United States Patent
Senn

[11] Patent Number: 5,989,321
[45] Date of Patent: Nov. 23, 1999

[54] CONDENSATE SEPARATOR WITH CONDENSATE REMOVAL

[75] Inventor: Jürgen Senn, Feldberg, Germany

[73] Assignee: Testo GmbH & Co., Lenzkirch, Germany

[21] Appl. No.: 09/041,939

[22] Filed: Mar. 13, 1998

[30] Foreign Application Priority Data

Mar. 14, 1997 [DE] Germany ............ 197 10 581

[51] Int. Cl.$^6$ .................................. B01D 45/08
[52] U.S. Cl. ............... 96/134; 55/392; 55/392.1; 55/423; 55/431; 55/466
[58] Field of Search ................ 55/392, 392.1, 55/423, 432, 430, 431, 428, 428.1, 466, 394, 395; 96/134

[56] References Cited

U.S. PATENT DOCUMENTS

| | | | |
|---|---|---|---|
| 523,929 | 7/1894 | Culver | 55/466 |
| 2,970,669 | 2/1961 | Bergson | 55/466 |
| 3,196,893 | 7/1965 | Stenger et al. | 137/204 |
| 3,225,524 | 12/1965 | Berrian | 55/428.1 |
| 4,547,130 | 10/1985 | Eastman | 55/466 |
| 4,600,416 | 7/1986 | Mann | 55/423 |

FOREIGN PATENT DOCUMENTS

| | | |
|---|---|---|
| 41 01 194 C1 | 1/1991 | Germany . |
| 42 41 891 A 1 | 12/1992 | Germany . |
| 51-98081 | 8/1976 | Japan . |
| 57-184405 | 11/1982 | Japan . |
| 63-12746 | 1/1988 | Japan . |
| 3-140699 | 9/1991 | Japan . |
| 700744 | 11/1979 | U.S.S.R. ............ 55/466 |
| 1346204 | 10/1987 | U.S.S.R. ............ 55/428 |

Primary Examiner—Duane S. Smith
Attorney, Agent, or Firm—Foley, Hoag & Eliot LLP

[57] ABSTRACT

A condensate separator for a portable (smoke) gas analyzer has a separating chamber formed inside a housing through which exhaust gasses pass. A condensate-collecting chamber is provided in hydraulic communication with the separating chamber and is at least partially filled with liquid absorbent material. The condensate removed from the exhaust gas is collected by the liquid absorbent material and wicked up through capillary action. Liquid is removed from the liquid absorbent material by a mechanical pump without requiring that the gas analyzer be stopped to drain out the condensate.

20 Claims, 7 Drawing Sheets

CONDENSATE SEPARATOR WITH CONDENSATE REMOVAL

BACKGROUND OF THE INVENTION

1. Field of the Invention

The invention relates to a condensate separator especially for a portable (smoke) gas analyzer, and more particularly to a condensate separator which provides for easy drainage of condensate.

2. Description of the Related Art

To analyze the flue gas from furnaces and the exhaust from gas engines for example, the gas to be measured is drawn in through a probe and fed to an analyzer. The gas to be measured must be prepared for gas analysis. In particular, smoke and dirt particles as well as moisture must be removed from the gas to be measured. It is therefore customary to provide a condensate separator to remove moisture from the gas to be measured to prevent condensate from entering the gas analyzer, and thus prevents condensate from contacting the sensors contained therein.

The basic design of such a condensate separator, as used especially in portable gas analyzers, is shown in DE 41 01 194 C1. This condensate separator has an especially simple design and is suitable for portable application.

In this condensate separator, the gas to be measured flows through a condensate separating chamber formed inside a housing and sealed off from the environment. The housing is tubular in shape and is sealed at both ends by plugs. The plugs are provided with nipples to connect to small tubes which form gas guide elements, so that gas can be guided into and out of the separating chamber.

The gas to be measured is introduced into the separating chamber on the influx side through the gas supply element. The moisture contained in the gas to be measured is separated in this separating chamber, with the separation taking place, for example, by multiple deflection of the stream of gas to be measured and as a result of the turbulence generated thereby. The gas to be measured, after being dehumidified in this fashion, leaves the separating chamber on the opposite side through the gas removal element and is fed to the analyzer. The separated condensate remains inside the separating chamber and precipitates on the housing walls. It is therefore necessary to remove the condensate manually at certain intervals. For this purpose, one of the two plugs is withdrawn from the housing so that the condensate contained therein can flow out of the housing. Depending on the quantity of condensate that accumulates, it may be necessary to repeat the emptying process at relatively short intervals. To allow a visual check by the operator, the housing is therefore made of a transparent material.

Another condensate separator is shown in DE 42 41 891 A1 from which the invention takes its departure. In this separator, a separating chamber is located inside the housing which has a gas supply element for introducing gas into the separating chamber as well as a gas removal element for removing gas from the separating chamber. In addition, the condensate separator has a condensate collecting chamber that is part of the separating chamber and receives the collected condensate. The condensate-collecting chamber enables simplified operation by virtue of the fact that it is possible to determine at any time, on the basis of the quantity of condensate contained in the condensate-collecting chamber, whether it is necessary to empty the chamber. In this case also, however, the emptying process must be performed manually. In addition, as in the case of the condensate separator described at the outset, it is unavoidable that the measuring process must be interrupted to remove the condensate. This is problematic, especially when measurements must be conducted continuously over long periods of time and with a large quantity of condensate collecting at the same time.

Hence the goal of the invention is to provide an improved condensate separator that permits condensate removal without opening the housing.

SUMMARY OF THE INVENTION

The invention is based on the idea of integrating liquid-absorbent material in the condensate-collecting chamber and draining the condensate that collects and is absorbed by the material into an external condensate removal element. The material that absorbs the liquid serves as a liquid buffer so that the emptying process needs to be performed by a suitable pump only at certain intervals, rather than continuously. On the other hand, the condensate contained in the housing can also be emptied practically completely when the absorptivity of the material located in the condensate-collecting chamber is exhausted and therefore additional condensate is precipitated unbound in the separating chamber. In an operating state of this kind, by initiating the suction process, condensate is drawn off from the fluid-absorbent material through the condensate removal element, and the condensate components that are initially free in the separating chamber are gradually absorbed by the liquid-absorbent material and then likewise removed. Operation of the condensate separator according to this invention is based largely on the capillary effect typical of the liquid absorbing material.

Preferably, the condensate-collecting chamber and the condensate removal element are components of a plug or of two plugs by which a tubular housing is sealed at both ends. In this manner it is possible to provide the condensate separator described at the outset with proven reliability, including suitably designed improvements, using the concept of condensate binding and removal according to the invention without changing the design otherwise. As a result, it also becomes possible to retrofit existing condensate separators of conventional design by replacing the plugs.

Preferably, two condensate-collecting chambers opposite one another are provided, each containing liquid-absorbent material. This makes it possible to achieve position-independent operation of the condensate separator. Changes in position during operation likewise do not affect functional reliability adversely since the condensate, depending on the current angular position, following any deviation from the horizontal, is necessarily fed to one or the other of the condensate-collecting chambers.

This version can be constructed extremely economically by using two similarly designed plugs each of which contains a condensate-collecting chamber and a condensate removal element. It goes without saying that in this case condensate must be pumped out of both condensate removal elements. This can be accomplished for example by using a simple hose pump and a switching valve so that both condensate-collecting chambers can be pumped out in sequence or alternately. It is also possible to use a hose pump with a double connection.

However, the version in which a liquid-transporting connection is created between the two condensate-collecting chambers is especially preferred. Additional liquid-absorbent material is preferably located inside a connecting tube that runs between the two condensate-collecting chambers. In this case it is sufficient to draw off the condensate through a single condensate-removal element, since condensate is also drawn out of the opposite condensate-collecting chamber by the capillary action of the material.

Additional preferred versions are directed at the specific embodiments of the condensate-collecting chamber in conjunction with the plugs that contain the gas guidance elements. For example, the condensate-collecting chamber may be preferably designed as an annular chamber between the annular outside wall of the plug and the gas guidance element that traverses the plug axially. As a result, the condensate-collecting chamber can be integrated without increasing the space requirements relative to those of the plugs known from the prior art.

The condensate-collecting chamber may be advantageously sealed axially from the outside by a disk-shaped cover, on which the condensate removal element is molded integrally. As a result, it is possible to connect the hose that leads to the pump without high construction cost. The endwise mounting on the condensate separator makes the connection readily accessible while increasing the volume of the condensate separator little if at all.

From a manufacturing standpoint, it is advantageous to press the cover tightly into a matching stepped bore in the plug. This type of connection allows economical manufacture of a plug which, following the insertion of the liquid-absorbent material and the subsequent pressing inward of the cover, can be mounted economically as a prefabricated assembly.

The communicating connection between the separating chamber and the condensate-collecting chamber is provided in simple fashion by virtue of the fact that at least one and preferably several bores uniformly distributed around the circumference are provided. The bores do not significantly weaken the structure of the plug and are sufficient to carry away the condensate that collects during operation to the condensate-collecting chamber.

Ideally an absorbent nonwoven material is used as the liquid-absorbent material, preferably a material based on viscose. This material is available economically in bulk and can be processed especially well. In addition it exhibits an excellent absorbency for liquids, with a simultaneously higher capillary action. An especially favorable feature is the property that the material expands after absorbing a comparatively small quantity of moisture and thus performs a sealing action, especially in the vicinity of the condensate removal element. A sealing effect of this kind is also especially desirable to eliminate leaking gas flows to the greatest extent possible.

Particular advantages are obtained when the condensate separator is drained by a hose pump. This has the advantageous property that it always allows the separating chamber and the condensate removal assembly to be sealed off from the environment.

BRIEF DESCRIPTION OF THE DRAWINGS

The preferred embodiments of the present invention will now be described more specifically with reference to the attached drawings, wherein:

FIGS. 2A–2C are a detailed diagrams of a plug, wherein

DETAILED DESCRIPTION OF THE PREFERRED EMBODIMENTS

Figure 1:
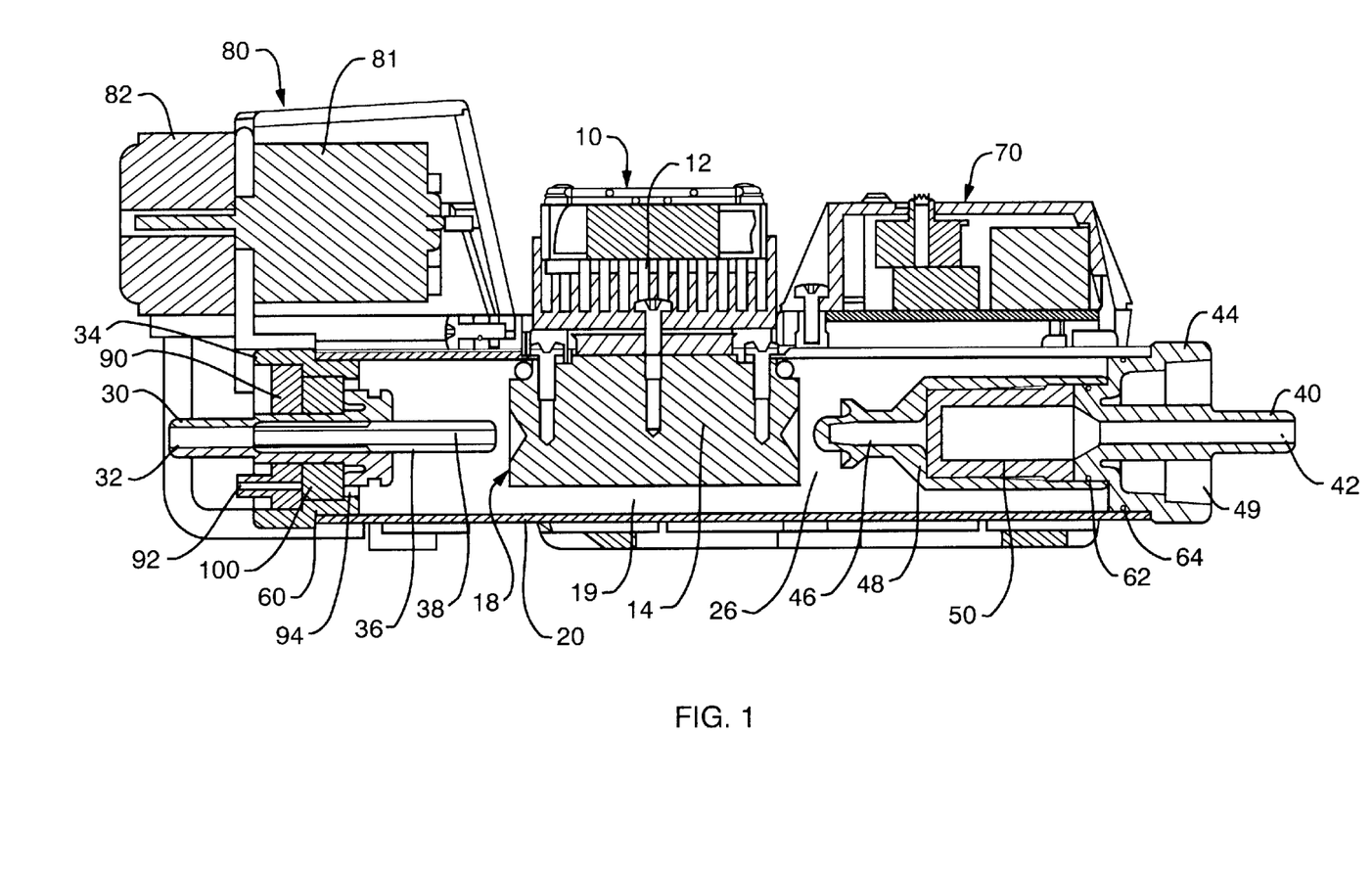
FIG. 1 is cross-sectional, axial section through a condensate separator.

As shown in FIG. 1, a condensate separator has a tubular housing 20 closed at opposite ends by plugs 34, 44 to form a separating chamber 26. Sealing rings 60, 64 are provided between plugs 34, 44 to ensure a tight seal between these elements.

A tubular gas supply element 30 is molded integrally on plug 34, which is traversed completely in the axial direction by a bore 32. A hose for the gas to be measured, not shown, can be connected to the gas supply element 30. A sampling probe can be mounted on the opposite end of this hose to collect exhaust gasses.

At the opposite end of the condensate separator, a tubular gas removal element 40 is molded in plug 44. The gas removal element 40 is traversed completely in the axial direction by a bore 42. A hose (not shown) can be connected to the gas removal element 40 to provide dehumidified gas to a gas analyzer.

A Peltier element 10 is inserted into tube 20 such that the warm side 12 of the Peltier element 10 is located outside tube 20 in known fashion to remove heat from the tube 20. A cold side 14 of the Peltier element 10 is mounted inside the tube 20. This cold side 14 of the Peltier element 10 projects almost completely into the separating chamber 26 and is designed to be used directly as a heat exchange surface for the gas to be measured as it flows through the tube. A radial gap 19 is left between the cold side 14 of the Peltier element 10 and the housing 20.

To improve condensate separation further, additional flow deflections are formed. For this purpose, plug 34 has a tap element 36 provided with an axial through bore 38. The tap element 36 extends concentrically with respect to the tube 20 and is guided axially close to the cold side 14 of the Peltier element 10. The gas to be measured, which escapes endwise from the tap element 36 through bore 38, thus strikes end 18 of the cold side 14 of Peltier element 10. End 18 thus acts as an impact surface. As a result of this impact, the gas to be measured is initially deflected opposite to the direction of impact before it is conducted through axial gap 19 following another deflection and is guided along the cold side 14 of the Peltier element 10.

Beyond cold side 14 of the Peltier element 10, a double deflection then takes place, caused by another tap element 46, supported by plug 44. This element also has a bore 48 extending coaxially with respect to tube 20. Tap element 46 is likewise brought close to cold side 14 of the Peltier element 10 so that the stream of gas to be measured is forced to change direction in order to enter bore 48. Bore 48 terminates inside tap element 46, which is sealed off from plug 44 by a sealing ring 62 and which has a filter 50 to separate particles. Hence, the unobstructed interior of tube 20 is available as separating chamber 26.

An electronic module 70 may be mounted externally on housing 20 to indicate and/or control operation of the condensate separator.

The condensate precipitated in the separating chamber 26 is transported out of the interior of the housing 20 through a condensate removal element 92. Condensate removal element 92 is designed as a hose nipple to which a hose 84 (see e.g. FIG. 3) can be fitted and can be connected to a hose pump 80 consisting of a drive motor 81 and hose cassette 82. Hose pump 80 is mounted externally on housing 20 to produce an especially compact design.

Figure 2A:
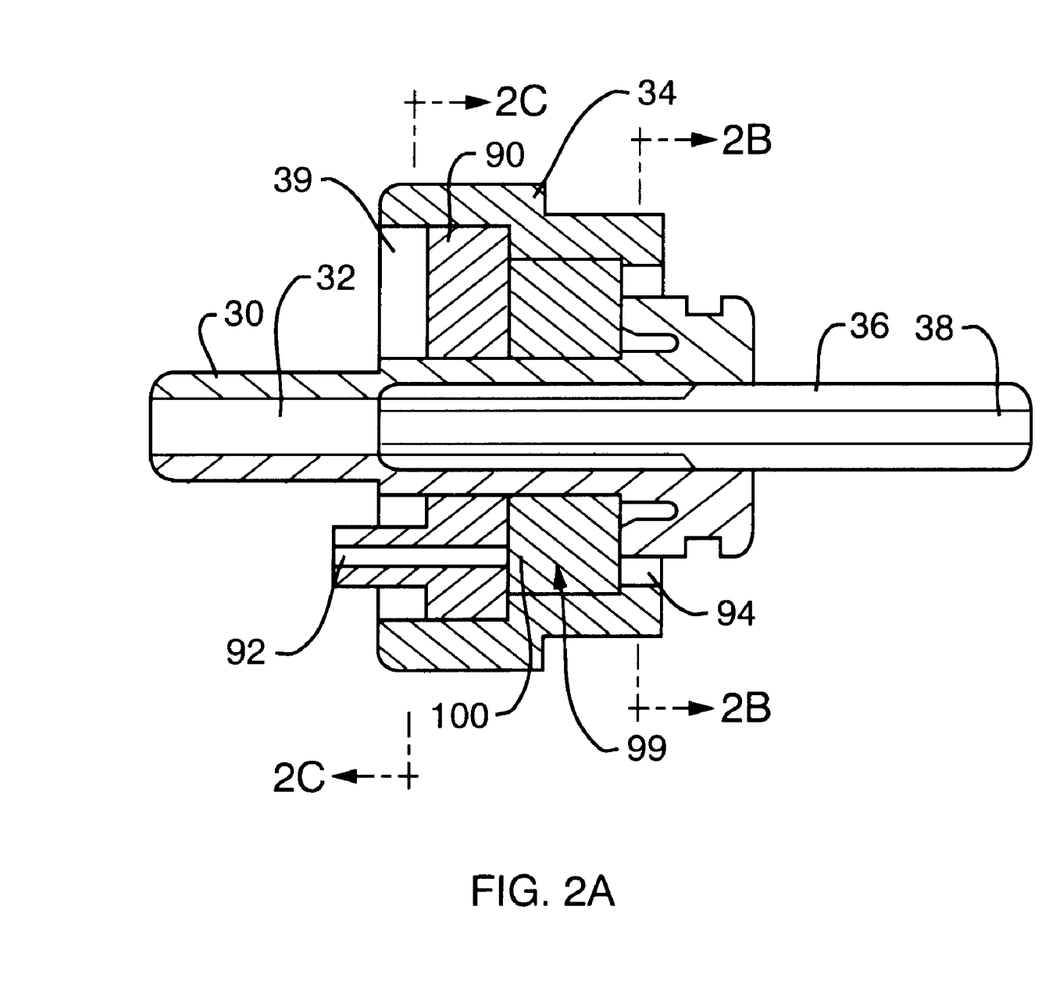
FIG. 2A is a cross-sectional view of a plug.
Figure 2B:
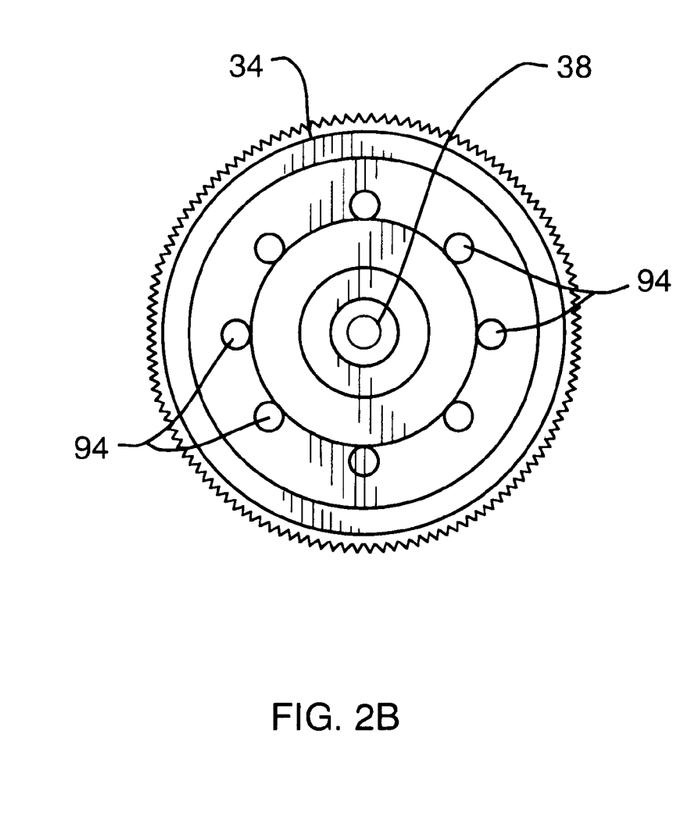
FIG. 2B is a cross-sectional view of the plug of FIG. 2A taken along line B—B.
Figure 2C:
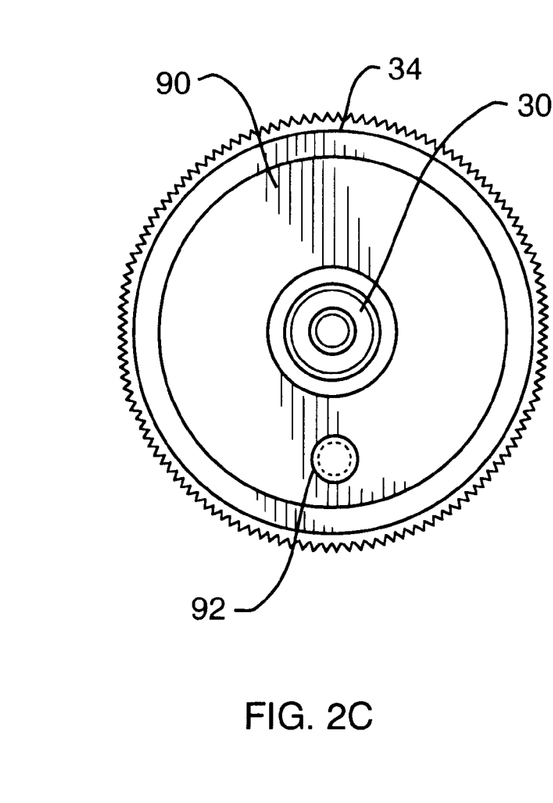
FIG. 2C is a cross-sectional view of the plug of FIG. 2A taken along line C—C.

As shown in more detail in FIGS. 2A–2C, a condensate-collecting chamber 99 is formed in the vicinity of plug 34 as an annular chamber between the annular outside wall of plug 34 and gas guide element 30 that traverses plug 34 axially. It is thus a part of an annular stepped recess 39 formed externally on plug 34. The condensate-collecting chamber 99 is filled almost entirely with a viscose nonwoven material that has a high capillary action and a high absorbency for liquids. The condensate-collecting chamber 99 is sealed externally by a disk-shaped cover 90 pressed tightly into a stepped recess 39 on plug 34. A hose nipple 92 is molded integrally on cover 90.

To form a hydraulic communication between the separating chamber 26 and the condensate-collecting chamber 99, eight bores 94, uniformly distributed around the circumference of the plug, are provided endwise on plug 34. The accumulating condensate is drawn through bores 94 as a result of the capillary action of nonwoven material 100, into condensate-collecting chamber 99 and is absorbed by non-woven material 100. The condensate is removed at certain intervals that essentially reflect the quantity of condensate that accumulates. For this purpose, hose pump 80 is operated, for example, under automatic control.

In this condensate separator, the condensate is removed unilaterally, in other words, in the vicinity of the location where the gas to be measured is introduced. Because of this arrangement, it is then possible to remove condensate when the condensate separator is held tilted at least slightly out of the horizontal toward the side where condensate-collecting chamber 99 is located. This facilitates the outward flow of condensate toward condensate-collecting chamber 99. The angular position relative to the lengthwise axis (rotational axis) is unimportant since the plurality of holes 34 located around the circumference in any case permits direct influx into condensate-collecting chamber 99.

Figure 3:
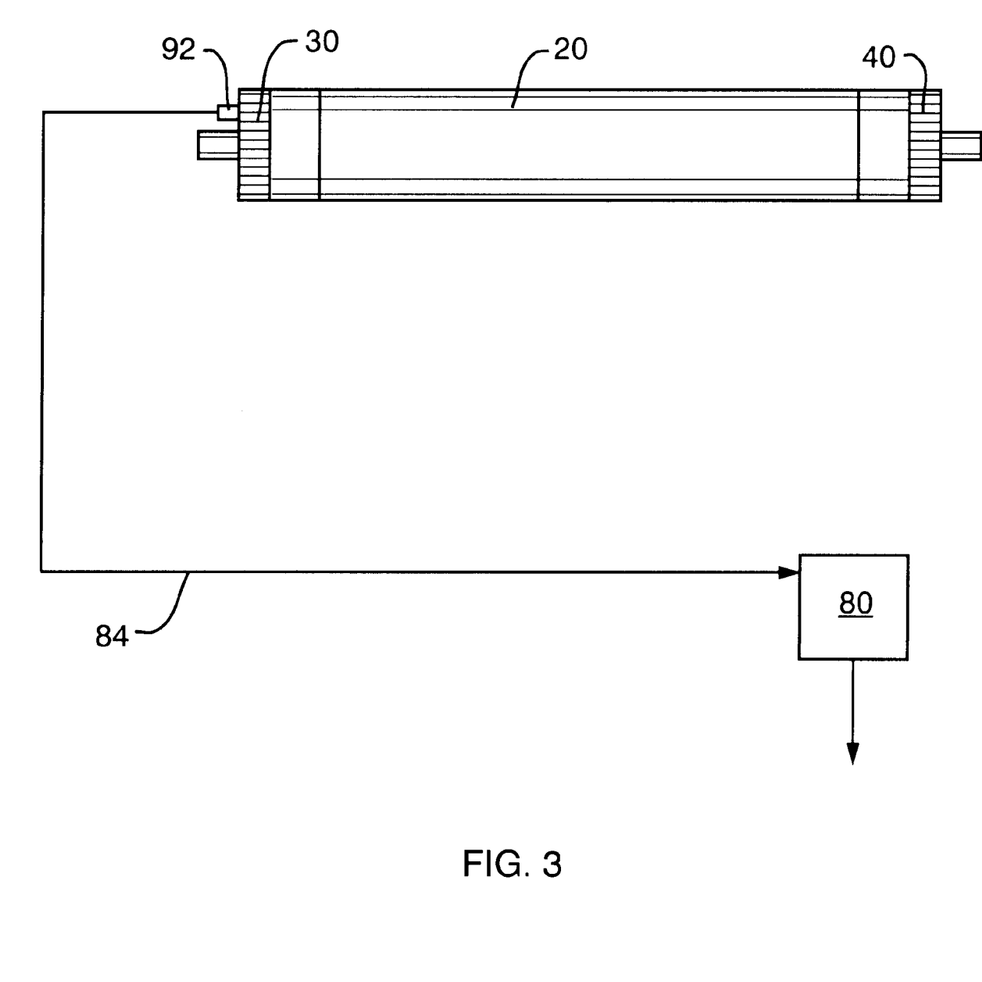
FIG. 3 is a schematic view of a condensate separator with condensate removal on one side with a single-acting hose pump.

The basic concept of unilateral condensate removal with a single-acting hose pump 80 is illustrated in FIG. 3 as well. This figure shows housing 20 sealed at both ends by plugs 30, 40. Only one of the two plugs, namely plug 30, has a hose nipple 92 to which hose 84 is connected, which is in turn connected to hose pump 80.

If it is desired to produce a completely position-independent condensate removal system, it is necessary to provide an additional condensate-collecting chamber 99 in the vicinity of plug 44. Plug 44 can be made basically identical to plug 30 and filter 50 can be eliminated. It is also readily possible to modify plug 44 in such fashion that it also can be used to absorb condensate. Plug 44 already possesses an annular stepped recess 49 designed to match stepped recess 39 of plug 34. Additional nonwoven material 100 can likewise be placed in stepped recess 49 and a cover 90 can be pressed in tightly. As an additional measure, it is merely necessary to provide through bores in suitable fashion to create the connection to separating chamber 26.

Figure 4:
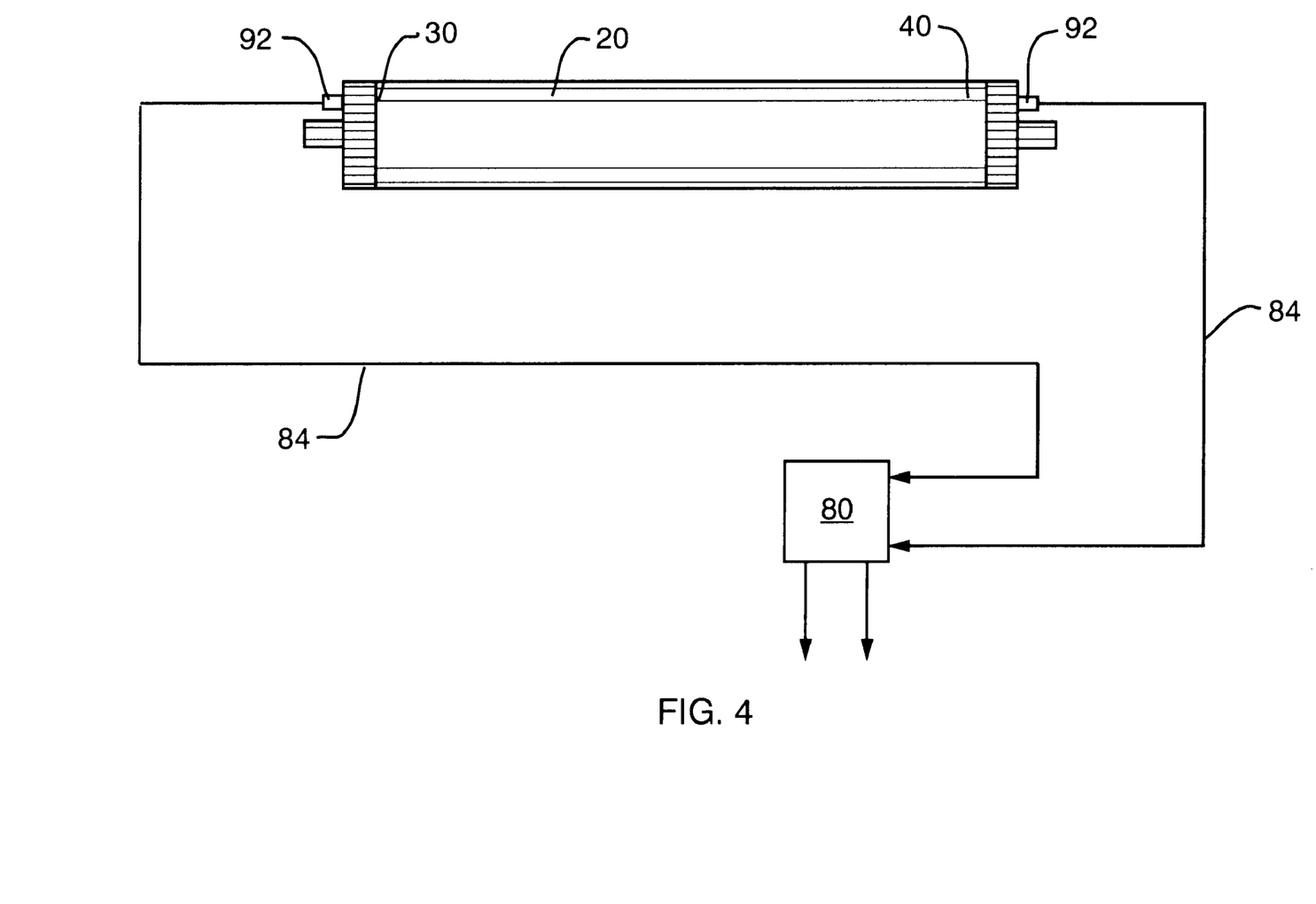
FIG. 4 is a schematic view of a condensate separator with bilateral condensate removal using a double-acting hose pump.

Condensate can be removed in two different ways. According to the version shown in FIG. 4, a hose nipple 92 is also provided in the vicinity of gas removal element 40, to which nipple a hose 84 is likewise connected. In addition, hose pump 80 is designed to be double-acting, in other words, both hoses 84 are operated in parallel so that the two condensate-collecting chambers 99 are emptied simultaneously.

Figure 6:
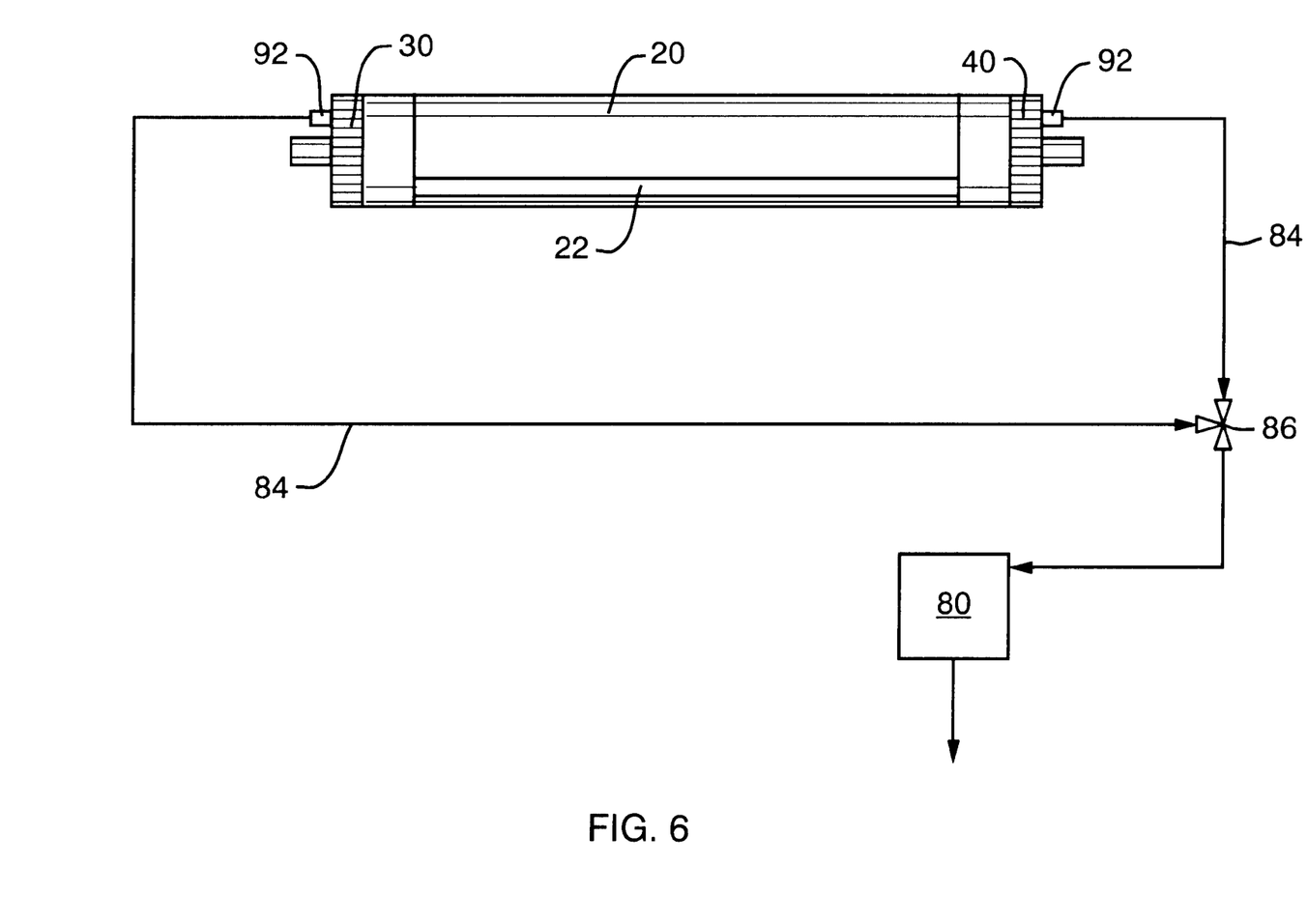
FIG. 6 is a schematic view of a condensate separator, with bilateral condensate removal, a single-acting hose pump, and a switching valve.

Alternatively, a single-acting hose pump 80 can be used, with the two hoses 84 being connected to a switching valve 86. This version is shown in FIG. 6. This version makes it possible to use a single-acting hose pump, with the two condensate-collecting chambers 99 being emptied successively or alternately by switching valve 86.

Figure 5:
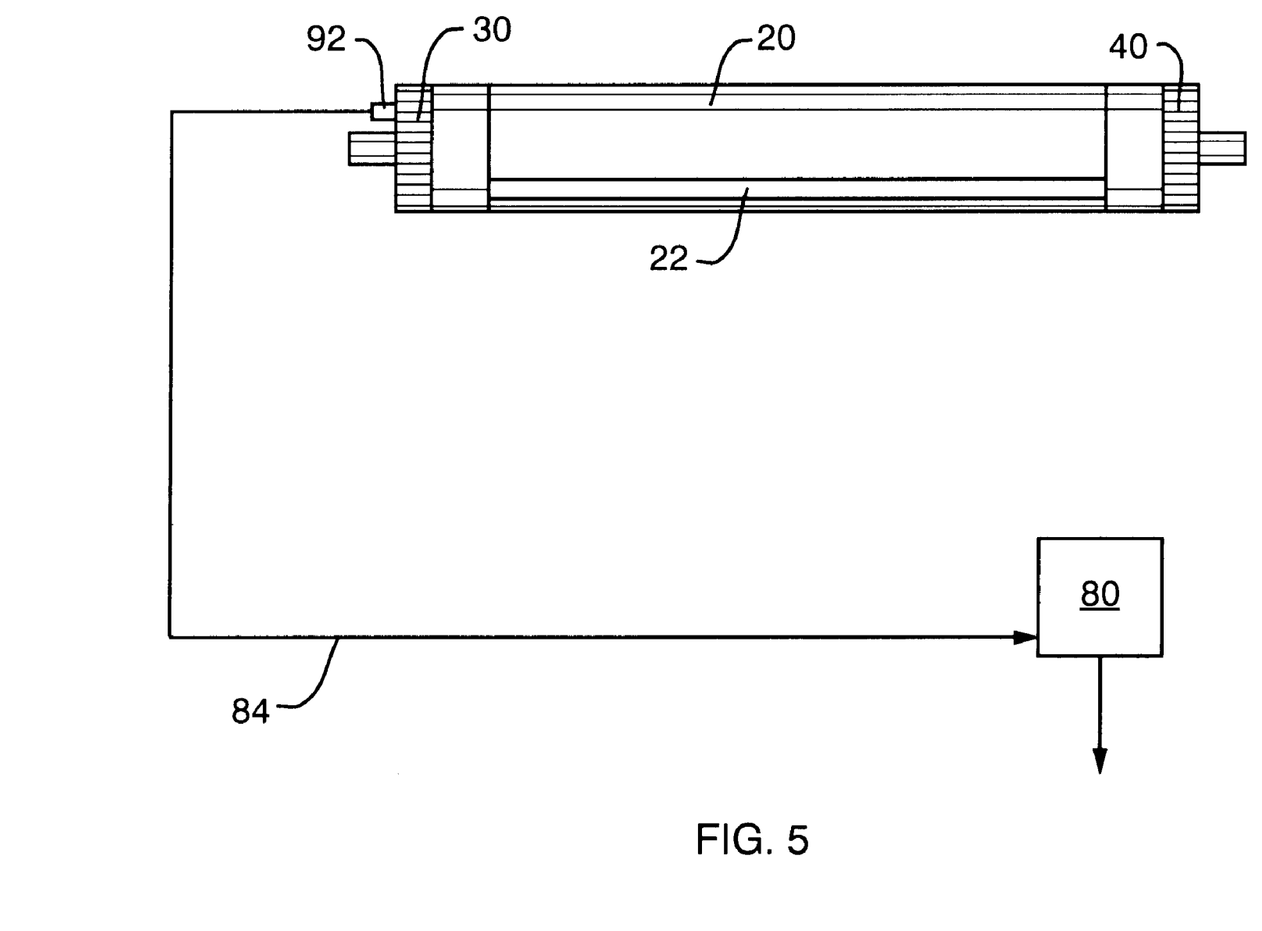
FIG. 5 is a schematic view of a condensate separator with unilateral condensate removal, a connecting tube, and a single-acting hose pump.

In a preferred embodiment, shown in FIG. 5, a single-acting hose pump 80 is provided to draw condensate off only one side of the condensate separator, for example, in the vicinity of gas supply element 30. Position-independent operation can be achieved in this case by providing a connecting tube 22 inside housing 20 to connect the two condensate-collecting chambers 99 with one another. Collecting tube 22 is likewise filled with nonwoven material so that a liquid-transporting connection from the condensate-collecting chamber 99 associated with gas removal element 40 to the opposite condensate-collecting chamber 99 is created, through which connection the condensate is removed. In this instance, a cover 90 must be used that has no connecting nipple 92, or the connecting nipple 92 should be tightly sealed.

Thus, it is possible to modify plugs 43 and/or 44 to enable condensate to be removed conveniently from the condensate separator. A conventional condensate separator can thus be retrofitted by simply replacing a plug as shown, for example, in FIG. 2.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

I claim:

1. A condensate separator, comprising:
    a housing defining a separating chamber for separating water vapor from a gas to be measured,
    a gas supply element disposed on the housing for guided the gas into the separating chamber,
    a gas removal element disposed on the housing for guiding gas out of the separating chamber,
    a first condensate-collecting chamber provided in hydraulic communication with the separating chamber, and
    liquid-absorbent material at least partially disposed within the first condensate-collecting chamber.

2. The condensate separator of claim 1, wherein the housing is tubular and is sealed at a first end by a first plug containing the gas supply element and is sealed at a second end by a second plug containing the gas removal element; and
    wherein the first condensate-collecting chamber is disposed within at least one of the first plug and the second plug.

3. The condensate separator of claim 1, further comprising a second condensate-collecting chamber opposite the first condensate collecting chamber and in hydraulic communication with the separating chamber, the second condensate-collecting chamber containing liquid-absorbent material.

4. The condensate separator according to claim 3, further comprising:
- a connecting tube in hydraulic communication between the first condensate-collecting chamber and the second condensate-collecting chamber; and
- liquid-absorbent material located inside the connecting tube to form a liquid-transporting connection between the first condensate-collecting chamber and the second condensate-collecting chamber.

5. The condensate separator of claim 2, wherein the first condensate-separating chamber is formed as an annular chamber between an annular outside wall of the first plug and the gas supply element.

6. The condensate separator of claim 2, wherein the first condensate-separating chamber is formed as an annular chamber between an annular outside wall of the second plug and the gas removal element.

7. The condensate separator of claim 5, further comprising a disk-shaped cover constructed and adapted to seal the condensate-collecting chamber axially from the outside, and on which a condensate removal element is molded integrally.

8. The condensate separator of claim 7, wherein the disk-shaped cover is pressed tightly into a matching stepped bore of the plug.

9. The condensate separator of claim 5, wherein at least one bore is formed in the first plug between the separating chamber and the first condensate-collecting chamber.

10. The condensate separator of claim 6, wherein at least one bore is formed in the second plug between the separating chamber and the second condensate-collecting chamber.

11. The condensate separator of claim 5, wherein a plurality of bores are formed in the first plug between the separating chamber and the first condensate-collecting chamber, the plurality of bores being uniformly distributed around the circumference of the first plug.

12. The condensate separator of claim 6, wherein a plurality of bores are formed in the second plug between the separating chamber and the second condensate-collecting chamber, the plurality of bores being uniformly distributed around the circumference of the second plug.

13. The condensate separator of claim 1, wherein the liquid-absorbent material is an absorbent, nonwoven material.

14. The condensate separator of claim 1, further comprising at least one condensate removal element disposed on said condensate separator in hydraulic communication with said first condensate-collecting chamber, and a hose pump connected with the condensate removal element.

15. A condensate separator, comprising:
- a housing defining a separating chamber having two ends;
- a plug disposed in one end of said separating chamber, said plug defining a passage for admitting gas there through and a condensate collecting chamber therein, said condensate collecting chamber being in hydraulic communication with said separating chamber and having a condensate removal element;
- a liquid-absorbent material at least partially disposed within said condensate collecting chamber.

16. The condensate separator of claim 15, further comprising:
- a pump operably associated with the condensate removal element to facilitate removal of condensate from the condensate collecting chamber.

17. The condensate separator of claim 15, further comprising: a second plug disposed in an end of said separating chamber opposite said plug, said second plug defining a passage for admitting gas there through and a second condensate collecting chamber therein, said condensate collecting chamber being in hydraulic communication with said separating chamber.

18. The condensate separator of claim 17, further comprising a connecting tube in hydraulic communication between said condensate collecting chamber and said second condensate collecting chamber.

19. The condensate separator of claim 18, further comprising liquid-absorbent material disposed within said connecting tube.

20. The condensate separator of claim 16, further comprising a second condensate removal element associated with said second condensate collecting chamber, and wherein said pump is operably associated with the second condensate removal element to facilitate removal of condensate from the second condensate collecting chamber.

* * * * *